(12) United States Patent
Lin et al.

(10) Patent No.: US 9,377,401 B2
(45) Date of Patent: Jun. 28, 2016

(54) BIOLOGICAL SENSING STRUCTURES

(71) Applicant: TAIWAN SEMICONDUCTOR MANUFACTURING COMPANY, LTD., Hsinchu (TW)

(72) Inventors: Hung-Hua Lin, Taipei (TW); Li-Cheng Chu, Taipei (TW); Ming-Tung Wu, Hsinchu (TW); Yuan-Chih Hsieh, Hsinchu (TW); Lan-Lin Chao, Sindian (TW); Chia-Shiung Tsai, Hsinchu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 103 days.

(21) Appl. No.: 14/491,255

(22) Filed: Sep. 19, 2014

(65) Prior Publication Data
US 2015/0044759 A1 Feb. 12, 2015

Related U.S. Application Data

(62) Division of application No. 13/372,141, filed on Feb. 13, 2012, now Pat. No. 8,846,129.

(51) Int. Cl.
G01N 21/00 (2006.01)
G01N 21/55 (2014.01)
G01N 27/327 (2006.01)
G01N 33/483 (2006.01)
G01N 21/01 (2006.01)
G01N 21/25 (2006.01)

(52) U.S. Cl.
CPC .............. *G01N 21/55* (2013.01); *G01N 21/01* (2013.01); *G01N 27/327* (2013.01); *G01N 33/483* (2013.01); *G01N 21/253* (2013.01); *G01N 2021/0106* (2013.01)

(58) Field of Classification Search
CPC ..... G01N 21/55; G01N 21/01; G01N 27/327; G01N 33/483; G01N 21/253; G01N 2021/0106
See application file for complete search history.

(56) References Cited

U.S. PATENT DOCUMENTS

| 7,309,620 | B2 | 12/2007 | Fonash et al. |
| 2004/0029303 | A1 | 2/2004 | Hart et al. |
| 2010/0099100 | A1 | 4/2010 | Zaccarin et al. |
| 2011/0222179 | A1 | 9/2011 | Monadgemi |

*Primary Examiner* — Dennis M White
(74) *Attorney, Agent, or Firm* — Slater Matsil, LLP

(57) ABSTRACT

A biological sensing structure includes a mesa integrally connected a portion of a substrate, wherein the mesa has a top surface and a sidewall surface adjacent to the top surface. The biological sensing structure includes a first light reflecting layer over the top surface and the sidewall surface of the mesa. The biological sensing structure includes a filling material surrounding the mesa, wherein the mesa protrudes from the filling material. The biological sensing structure includes a stop layer over the filling material and a portion of the first light reflecting layer. The biological sensing structure includes a second light reflecting layer over a portion of the stop layer and a portion of the top surface of the mesa. The biological sensing structure includes an opening in the second light reflecting layer to partially expose the top surface of the mesa.

20 Claims, 13 Drawing Sheets

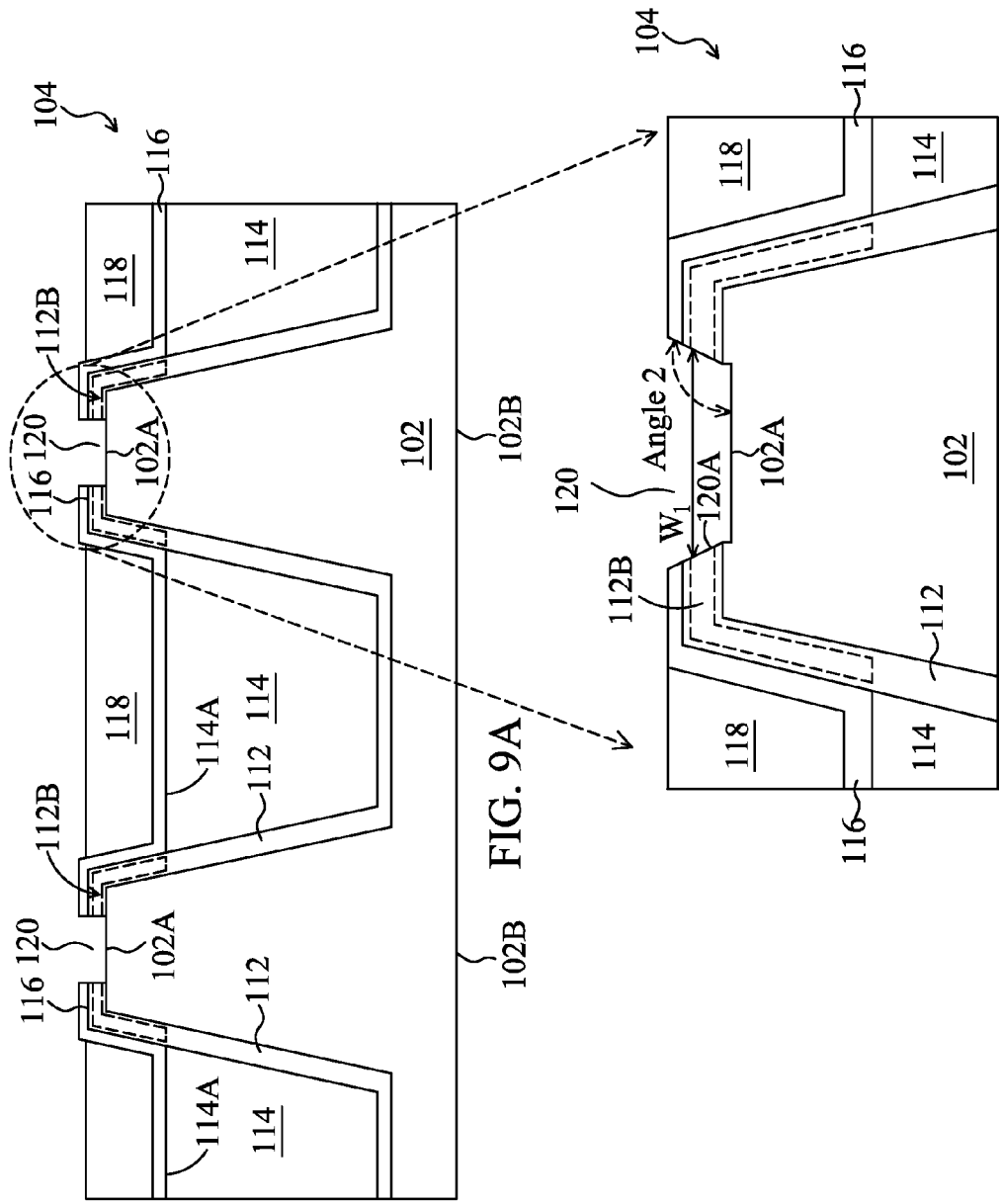

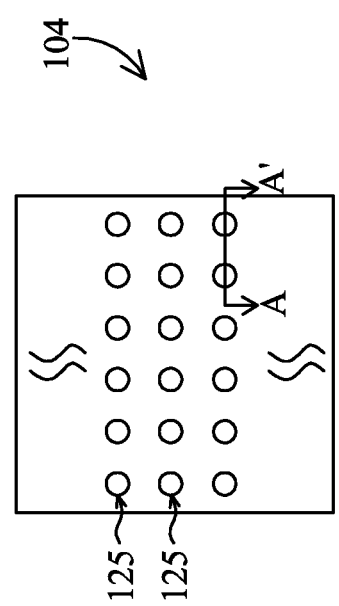

US 9,377,401 B2

BIOLOGICAL SENSING STRUCTURES

PRIORITY CLAIM

The present application is a divisional of U.S. application Ser. No. 13/372,141, filed Feb. 13, 2012, which is incorporated herein by reference in its entirety.

TECHNICAL FIELD

This disclosure relates to biological sensing structures.

BACKGROUND

Biological sensing structures or Biosensors are devices for sensing and detecting biomolecules and operate on the basis of electronic or optical detection principles. An advantage of biological sensing structures is the prospect of label-free operation. Specially, biological sensing structures enable the avoidance of costly and time-consuming labeling operations such as the labeling of an analyte with, for example, fluorescent or radioactive agents.

Biological sensing structures or biosensors can be manufactured using semiconductor processes. Biological sensing structures can quickly detect electrical or optical signals and can be easily applied to integrated circuits (ICs) and micro electro mechanical systems (MEMS). Despite the attractive properties noted above, a number of challenges exist in connection with developing biosensors. Various techniques directed at configurations and methods of forming these biosensors have been implemented to try and further improve device performances.

BRIEF DESCRIPTION OF THE DRAWINGS

Aspects of the present disclosure may be understood from the following detailed description and the accompanying figures. It is emphasized that, in accordance with the standard practice in the industry, various features are not drawn to scale. In fact, the dimensions of the various features may be arbitrarily increased or reduced for clarity of discussion.

FIGS. 4 to 11B are cross-sectional views of the structure of the biological chip having a biological sensing structure at various stages of manufacture according to various embodiments of the method of FIG. 2.

FIG. 12 is a top view of the single biological chip of FIG. 1B having a plurality of biological sensing structures formed in an arrangement of an array.

DETAILED DESCRIPTION

It is to be understood that the following disclosure provides many different embodiments, or examples, for implementing different features of the invention. Specific examples of components are arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiment in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

Figure 1:
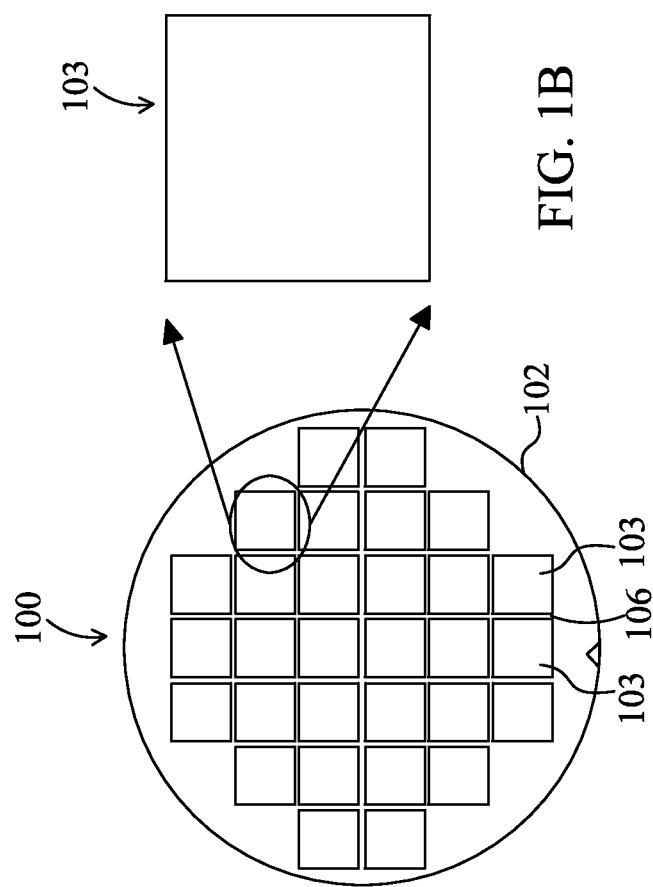
FIG. 1A is a top view of a wafer including a plurality of biological chips on a substrate according to one or more embodiments of this disclosure.
FIG. 1B is an enlarged view of a single biological chip of FIG. 1A according to one or more embodiments of this disclosure.

FIG. 1A is a top view of a wafer 100 including a plurality of biological chips 103 marked on a substrate 102. The plurality of biological chips 103 are divided by scribe lines 106 between the biological chips 103. FIG. 1B is an enlarged view of a single biological chip 103 depicted in FIG. 1A. The substrate 102 will go through a variety of cleaning, layering, patterning, etching or doping steps to form biological sensing structures in the biological chips 104. The term "substrate" herein generally refers to a bulk substrate that is suitable for transmitting electrical or optical signals of an analyte. In at least one example, the substrate includes a transparent material, such as quartz, sapphire, fused silica or other suitable glasses. In another example, the substrate is a rigid material which keeps the observed analyte in fixed positions during observation. In yet another example, the substrate is a transparent organic material, for example, methacrylate polymers such as PMMA, polycarbonates, cyclic olefin polymers, styrenic polymers, fluorine-containing polymers, polyesters, polyetherketones, polyethersulfones, polyimides or mixtures thereof. In some embodiments, various layers and devices structures are formed over the substrate. Examples of such layers include dielectric layers, doped layers, polysilicon layers or conductive layers. Examples of device structures include transistors, resistors, and/or capacitors, which may be interconnected through an interconnect layer to additional devices.

Figure 2:
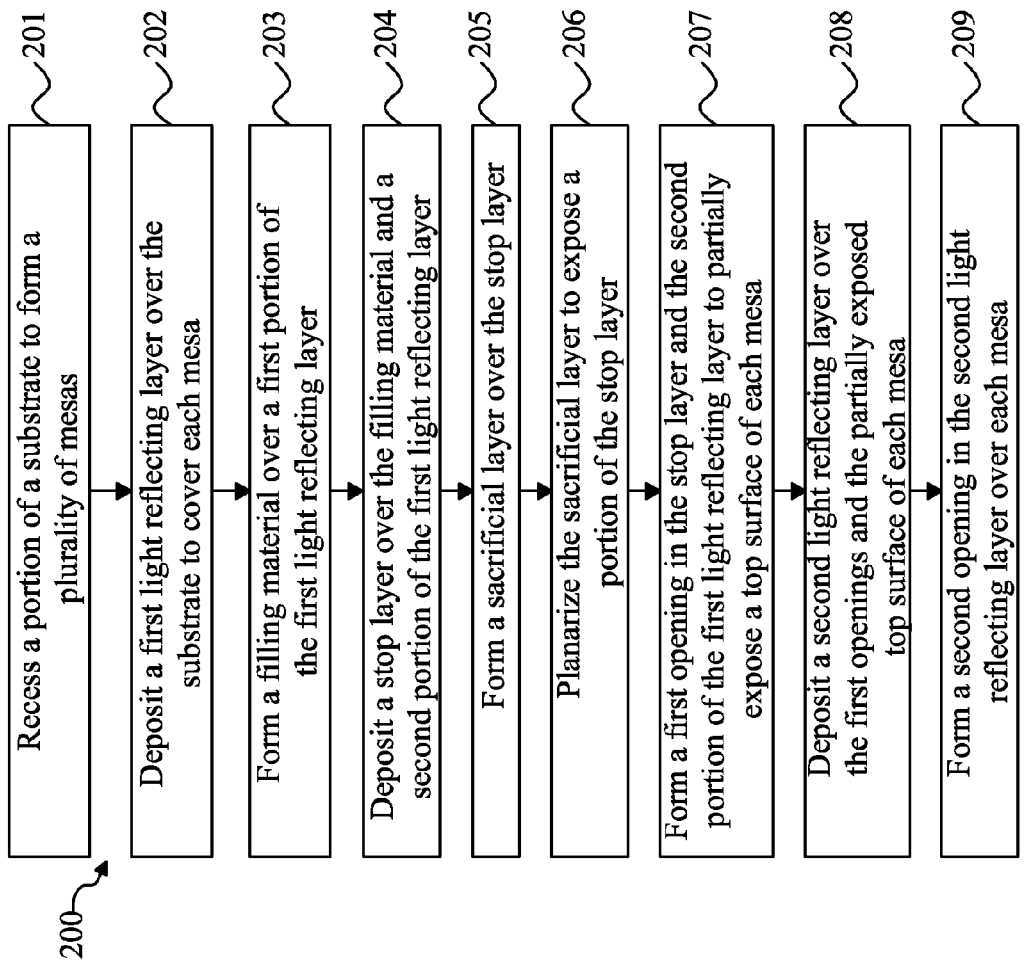
FIG. 2 is a flowchart of a method of forming a structure of a biological chip having a biological sensing structure according to one or more embodiments of this disclosure.

FIG. 2 is a flowchart of a method 200 of forming a structure of a biological chip having a biological sensing structure according to one or more embodiments of this disclosure. The method 200 may include forming the biological sensing structure using one or more process steps compatible with a complementary metal-oxide-semiconductor (CMOS) process. It is understood that the method 200 includes steps having features of a typical CMOS technology process flow and thus, are only described briefly herein. Further, it is understood that additional steps can be provided before, during, and after the method 200. Some of the steps described below can be replaced or eliminated for additional embodiments of the method 200. FIGS. 4 to 11 are cross-sectional views of a structure 104 of a biological chip having a biological sensing structure at various stages of manufacture according to various embodiments of the method 200 of FIG. 2. Various figures have been simplified for a better understanding of the inventive concepts of the present disclosure.

Figure 4:
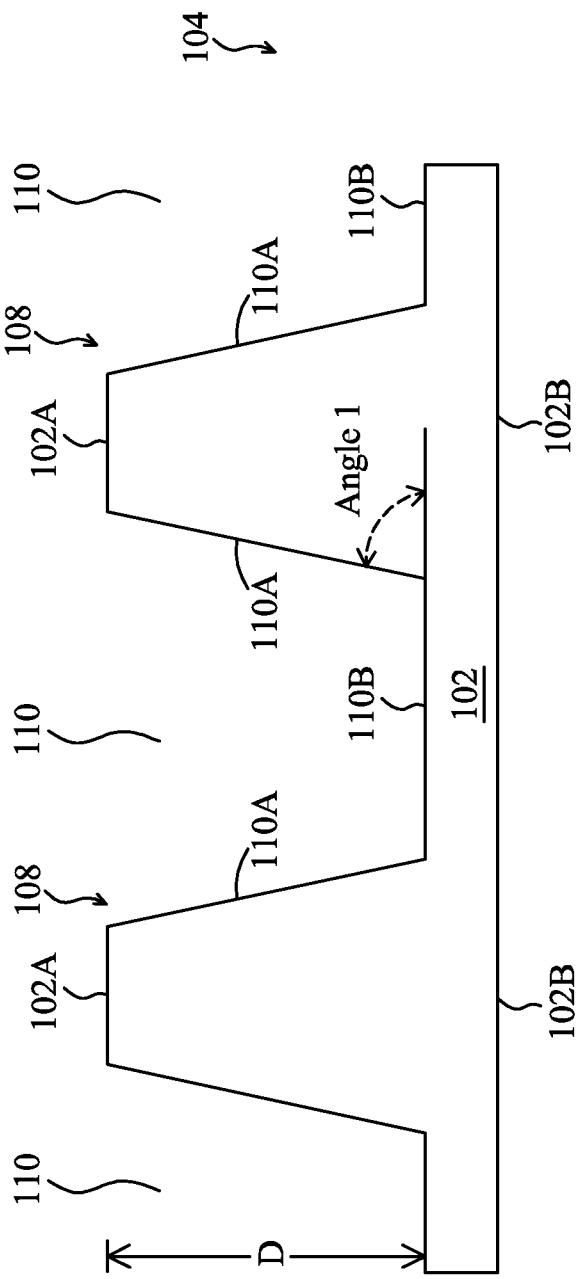

Referring to FIGS. 2 and 4, the method 200 begins with operation 201 in which a portion of a substrate is recessed to form a plurality of mesas. The recess operation may be formed by using suitable photolithography process to provide a pattern on the substrate. Then, etching processes are performed to remove a portion of the substrate to define the plurality of mesas. The adjacent mesas are separated by a recess. The etching processes may include wet etch, dry etch, plasma etch and/or other suitable processes.

Figure 3B:
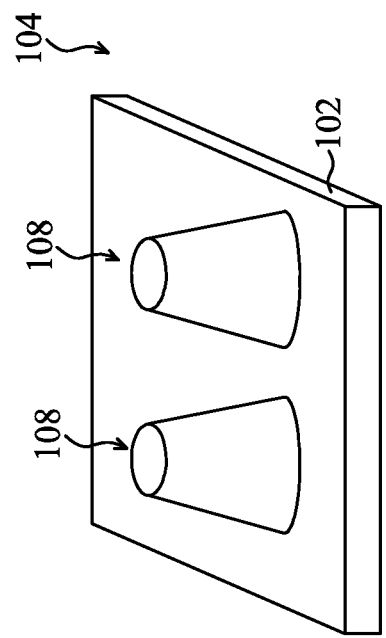
FIG. 3B is a perspective view of the single biological chip along line A-A' in FIG. 3A according to one or more embodiments of this disclosure.
Figure 3A:
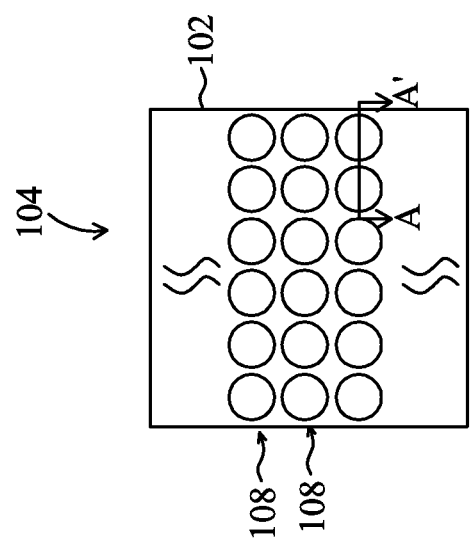
FIG. 3A is a top view of a structure of the single biological chip of FIG. 1B according to one or more embodiments of this disclosure.

Referring the example of FIG. 4, a portion of a substrate 102 is recessed to form a plurality of mesas 108. The recessed portion of the substrate 102 forms a plurality of recesses 110 surrounding each mesa 108. The adjacent mesas 108 are separated by a recess 110. In one embodiment, the mesas 108 are in an arrangement of an array as shown in FIG. 3A with a top view of the structure 104 of the biological chip. FIG. 3B is a perspective view of the mesas 108 along line A-A' in FIG. 3A. FIG. 4 is the cross-sectional view of the mesas 108 along line A-A' in FIG. 3A. The substrate 102 has a top surface 102A and a bottom surface 102B. The recesses 110 extend from the top surface 102A into the substrate 102 with a depth D of about 6 µm to 7 µm, while not penetrating through the bottom surface 102B. The recess 110 has an interior surface 110A and a bottom surface 110B. The mesa 108 has a top surface and a sidewall surface adjacent to the top surface. The top surface of the mesa 108 is the same as the top surface 102A of the substrate 102. The sidewall surface of the mesa 108 is the same as the interior surface 110A of the recess 110. In one example, the mesa 108 has an interior angle, Angle 1, between a plane parallel to the bottom surface 110B and the interior surface 110A, from about 60° to about 85°. In another example, the mesa 108 has the interior angle, Angle 1, from about 75° to about 85°.

Figure 5:
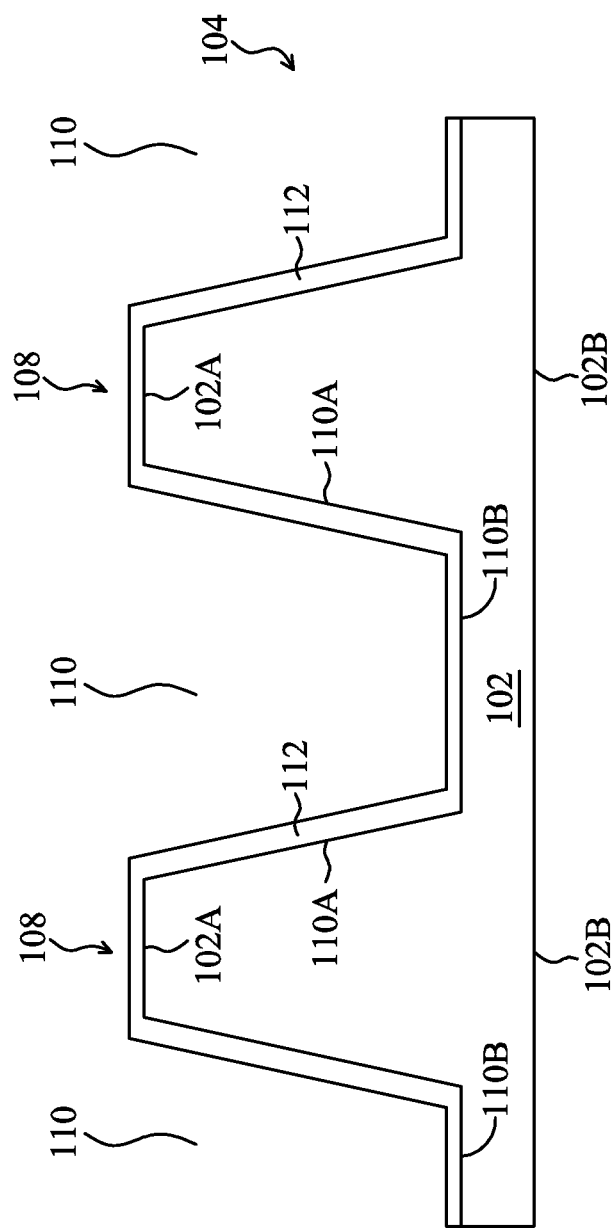

Referring to FIGS. 2 and 5, the method 200 continues with operation 202 in which a first light reflecting layer is deposited over the substrate to cover each mesa. The first light reflecting layer includes a metallic material such as aluminum, copper, gold, silver, chrome, or mixtures thereof. The first light reflecting layer may be formed by a suitable process, such as physical vapor deposition (PVD), chemical vapor deposition (CVD) or atomic layer deposition (ALD). The first light reflecting layer can also comprise a reflective organic polymer, such as a composite material comprising reflective particles dispersed in a polymeric material.

Figure 13:
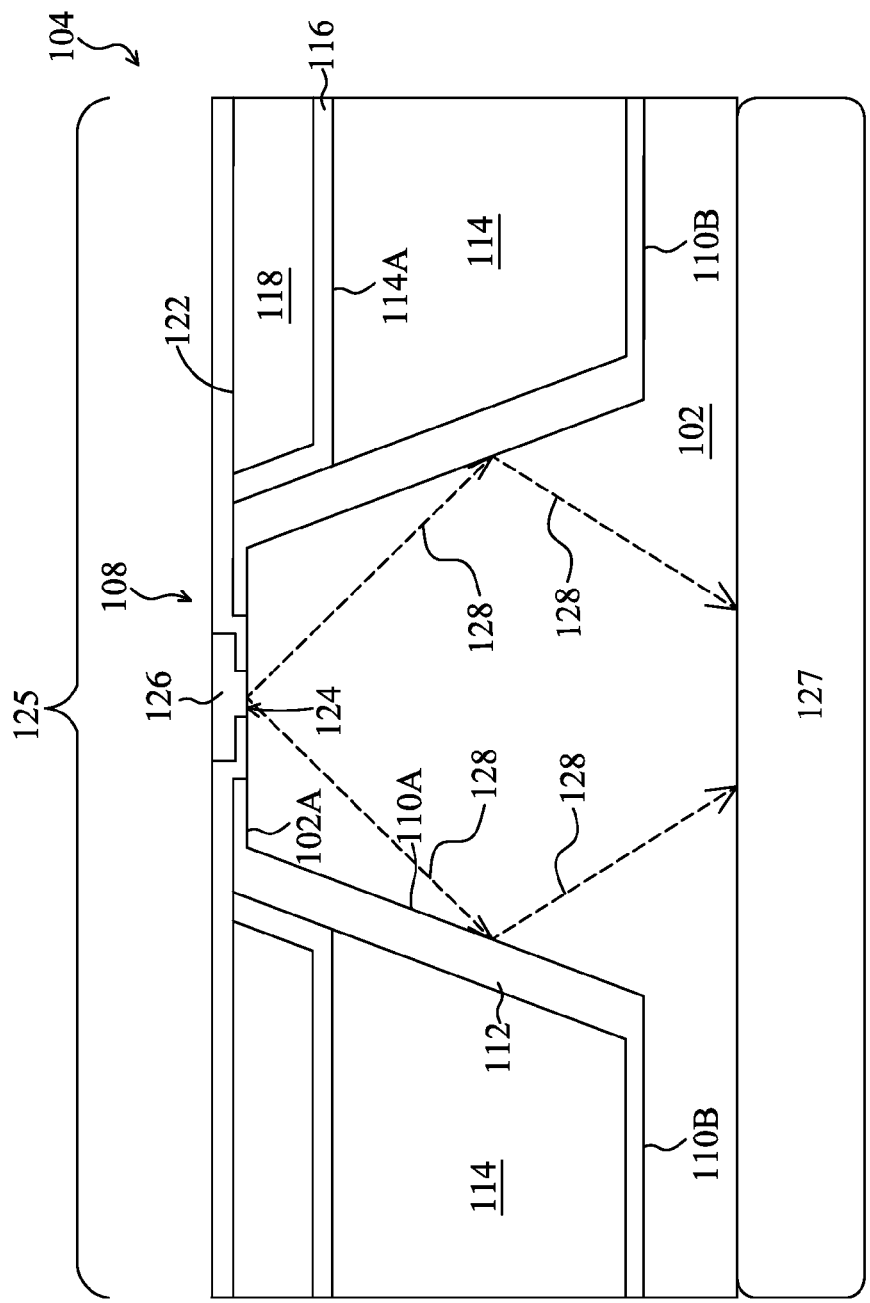
FIG. 13 illustrates an enlarged cross-sectional view of a biological sensing structure in an operation of detecting biomolecules.

Referring the example of FIG. 5, a first light reflecting layer 112 is deposited over the substrate 102 to cover the top surface 102A and the interior surface 110A of each recess 110, and the bottom surface 110B of the recesses 110. In one example, the first light reflecting layer 112 has a thickness ranging from about 1000 Å to about 3000 Å. The mesa 108 and the first light reflecting layer 112 disposed on an outside surface (102A and 110A) of the mesa 108 is configured as a micro-minor. The first light reflecting layer 112 may enhance the reflectivity of the outside surface (102A and 110A) of the mesa 108. The operation of the micro-mirror will be explained further in the later section as shown in FIG. 13.

Figure 6:
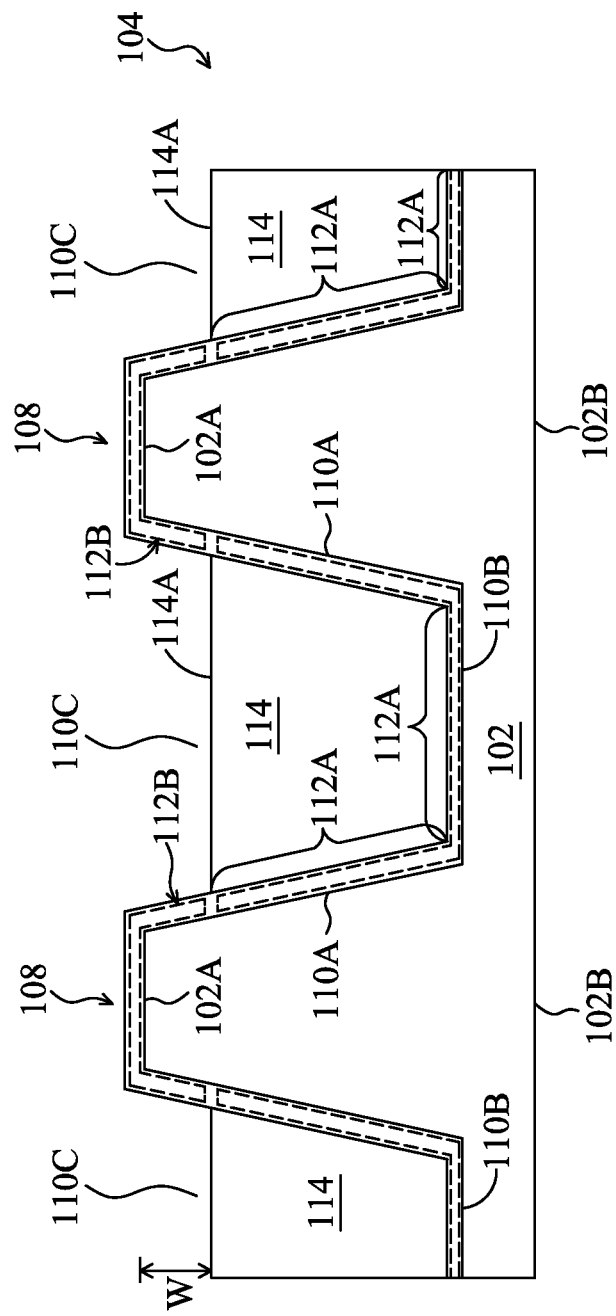

Referring to FIGS. 2 and 6, the method 200 continues with operation 203 in which a filling material is formed over a first portion of the first light reflecting layer to expose a second portion of the first light reflecting layer. In some embodiments, the filling material includes silicon oxide, low k dielectric material or other suitable dielectric materials. The filling material is formed by low temperature chemical vapor deposition (LTCVD) at an operation temperature less than 300° C. to prevent damaging the substrate for electrical or optical signals detection. In at least another embodiment, the filling material may include PMMA, polycarbonates, cyclic olefin polymers, styrenic polymers, fluorine-containing polymers, polyesters, polyetherketones, polyethersulfones, polyimides or mixtures thereof deposited by spin coating.

In at least one embodiment, the filling material is formed on the substrate to a level above top surfaces of the mesas and the first light reflecting layer. A planarization process, such as a chemical mechanical polishing (CMP) process and/or an etching process, is applied to the filling material to reduce the thickness of the filling material to expose the second portion of the first light reflecting layer. In one embodiment, the planarized filling material partially fills each recess between adjacent mesas and leaves remaining recesses. The planarized filling material has a top surface lower than the top surface of each mesa. The second portion of the first light reflecting layer on each mesa protrudes from the top surface of the surrounding filling material. Each remaining recess has a depth W between the top surface of each mesa and the top surface of the planarized filling material.

Referring the example of FIG. 6, a filling material 114 partially fills the recesses 110 surrounding each mesa 108 and leaves remaining recesses 110C. The filling material 114 has a top surface 114A lower than the top surface 102A of each mesa 108. A first portion 112A of the first light reflecting layer 112 is embedded in the filling material 114. A second portion 112B of the first light reflecting layer 112 on the top surface 102A of the mesa 108 and a top portion of the sidewall surface 110A of the mesa 108 is exposed from the filling material 114. A depth W of the remaining recess 110C is less than about 6000 Å.

Figure 7:
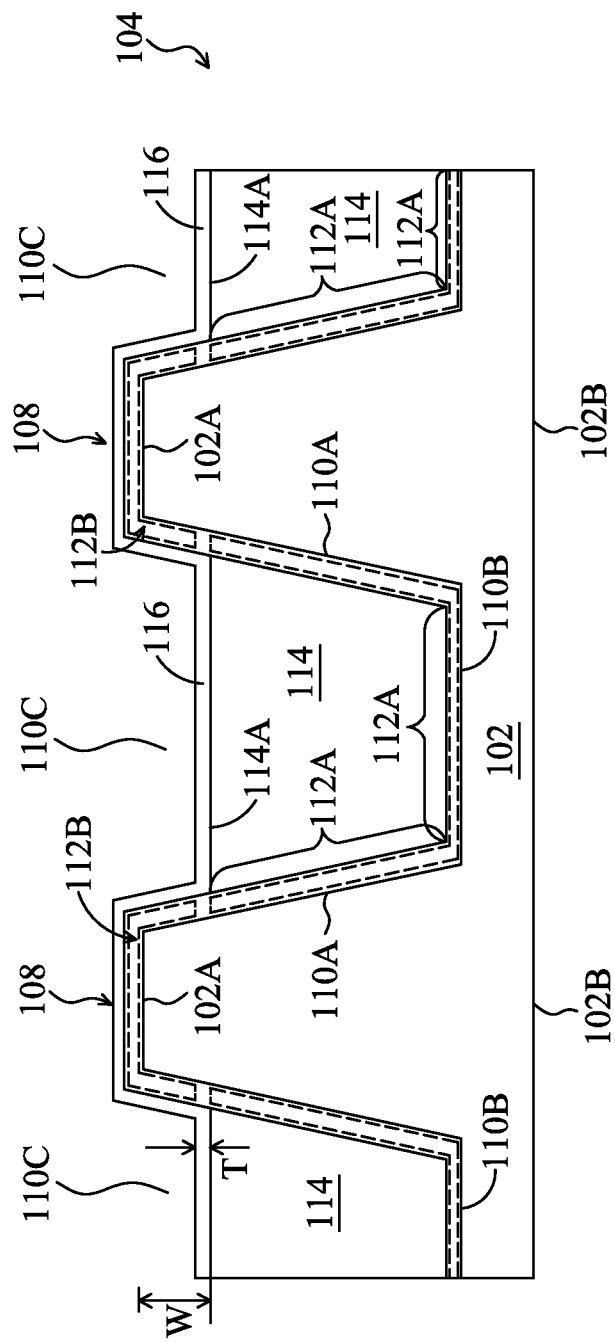

Referring to FIGS. 2 and 7, the method 200 continues with operation 204 in which a stop layer is deposited over the filling material and the second portion of the first light reflecting layer. In some embodiments, the stop layer includes silicon oxide, silicon nitride, silicon oxy-nitride or other suitable materials which have higher etching or polishing resistance compared to a following formed sacrificial layer. In some examples, the stop layer is a conformal liner along the top surface of the filing material and the second portion of the first light reflecting layer. The stop layer has a thickness T less than the depth W of the remaining recesses. The stop layer may be formed by plasma enhanced chemical vapor deposition (PECVD), high aspect ratio process (HARP), ALD or a spin on dielectric (SOD).

Referring the example of FIG. 7, a stop layer 116 is deposited over the filling material 114 and the second portion 112B of the first light reflecting layer 112. In some embodiments, the stop layer 116 is a conformal liner along the top surface 114A of the filing material 114 and the second portion 112B of the first light reflecting layer 112, and does not overfill the remaining recesses 110C. The stop layer 116 has a thickness T less than the depth W of the remaining recesses 110C. The thickness T is in a range of about 1000 Å to about 2500 Å. A ratio of the depth W to the thickness T is larger than about 5. The stop layer 116 may include silicon oxide, silicon nitride, silicon oxy-nitride, or other suitable materials which have higher etching or polishing resistance compared to a following formed sacrificial layer 118.

Referring back to FIG. 2, the method 200 continues with operation 205 in which the sacrificial layer is formed over the stop layer to a level above a top surface of the stop layer over the mesas. Namely, the sacrificial layer overfills the remaining recesses. In one embodiment, the sacrificial layer includes polycrystalline silicon, amorphous silicon or other suitable materials which have less etching or polishing resistance compared to the stop layer formed in operation 204. The sacrificial layer may be formed by CVD, PECVD or low pressure chemical vapor deposition (LPCVD).

Figure 8:
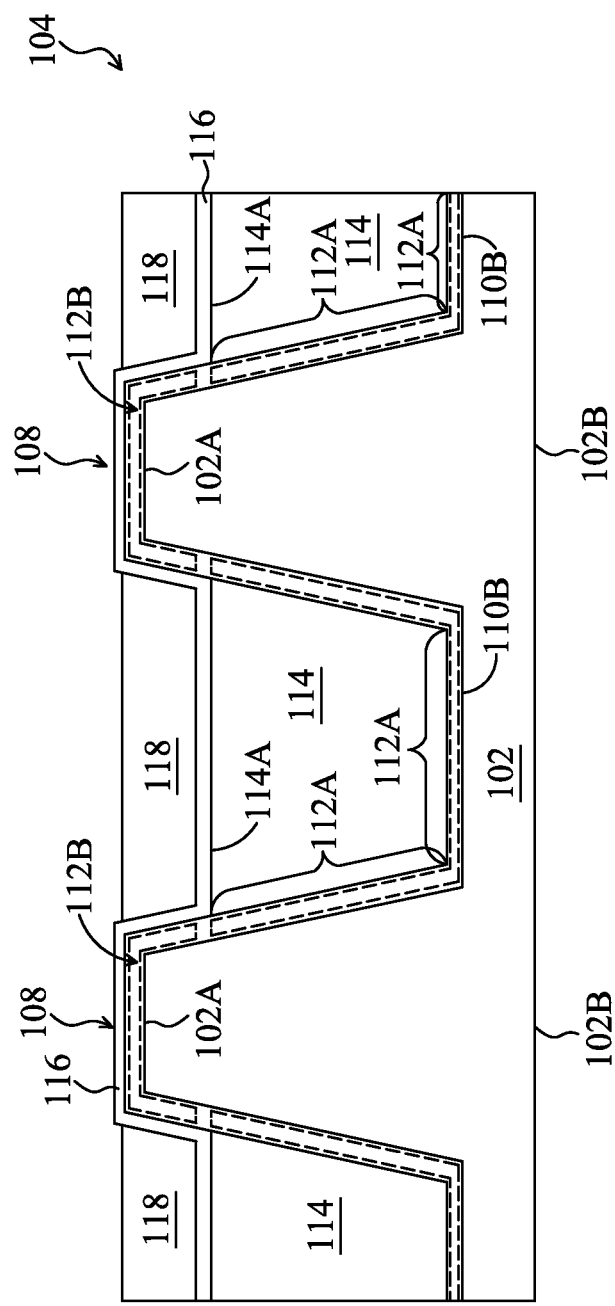

Referring to FIGS. 2 and 8, the method 200 continues with operation 206 in which the sacrificial layer is planarized to expose a portion of the stop layer. A planarization operation, such as a chemical mechanical polishing (CMP) process and/or an etching process, is applied to the sacrificial layer to reduce the thickness of the sacrificial layer to expose a portion of the stop layer. In some embodiments, the process conditions and parameters of the CMP process, including slurry chemical and polishing pressure, are tuned to planarize the sacrificial layer. The stop layer has higher etching or polishing resistance compared to the sacrificial layer in operation 206. The planarization operation 206 could cease as the top surface of the stop layer is exposed. In at least one example, a removed rate ratio of the sacrificial layer to the stop layer is larger than about 100. In at least another example, the removed rate ratio of the sacrificial layer to the stop layer is larger than about 400. In some embodiments, a top surface of the planarized sacrificial layer and the top surface of the stop layer over the mesas have a step height less than 3000 Å. In at least another embodiment, the top surface of the planarized sacrificial layer is substantially planar to the top surface of the stop layer over the mesas. Advantageously, use of the stop layer improves the uniformity of the planarized surface of the sacrificial layer. The planarized sacrificial layer and the top surface of the stop layer over the mesas get a smooth new surface. The smooth new surface would achieve a better resolution for the following lithography process on the new surface. The device performance and yield on the completed products are thus significantly increased.

Referring the example of FIG. 8, the structure 104 of the biological chip illustrates a cross-sectional view after performance of operations 205 and 206. A sacrificial layer 118 is formed over the stop layer 116 and planarized. A portion of the stop layer 116 over each mesa 108 is exposed. In some embodiments, a top surface of the planarized sacrificial layer and the top surface of the stop layer over the mesas have a step height (not shown) less than 3000 Å. In another embodiment, the top surface of the planarized sacrificial layer 118 is substantially planar to the top surface of the stop layer 116 over the mesas 108.

Referring to FIGS. 2 and 9A, the method 200 continues with operation 207 in which a first opening is formed in the stop layer and the second portion of the first light reflecting layer to partially expose a top surface of each mesas. The first opening forming operation may be formed by using suitable photolithography process to provide a pattern on the stop layer. The patterned stop layer is then subjected to etching processes to remove a portion of the stop layer and the first light reflecting layer to define the first opening.

Referring the example of FIG. 9A, a first opening 120 is formed in the stop layer 116 and the second portion 112B of the first light reflecting layer 112 to expose a portion of the top surface 102A of each mesa 108. FIG. 9B illustrates an enlarged cross-sectional view of a portion of the structure 104 of the biological chip in FIG. 9A. In at least one example, the first opening 120 has a width $W_1$ and an interior angle, Angle 2, between the top surface 102A and a tapered sidewall 120A, greater than 90°. In at least another example, the interior angle, Angle 2, is greater than about 100°. In some embodiments, the first light reflecting layer 112 is aluminum. The aluminum layer is etched with a plasma process in a $BCl_3/Cl_2$ ambient environment. A gas ratio of $BCl_3/Cl_2$ is in a range from about 0.5 to about 1.3. Within this gas ratio, the first opening 120 has the tapered sidewall 120A with the interior angle, Angle 2, greater than 90°.

Figures 10A, 10B:
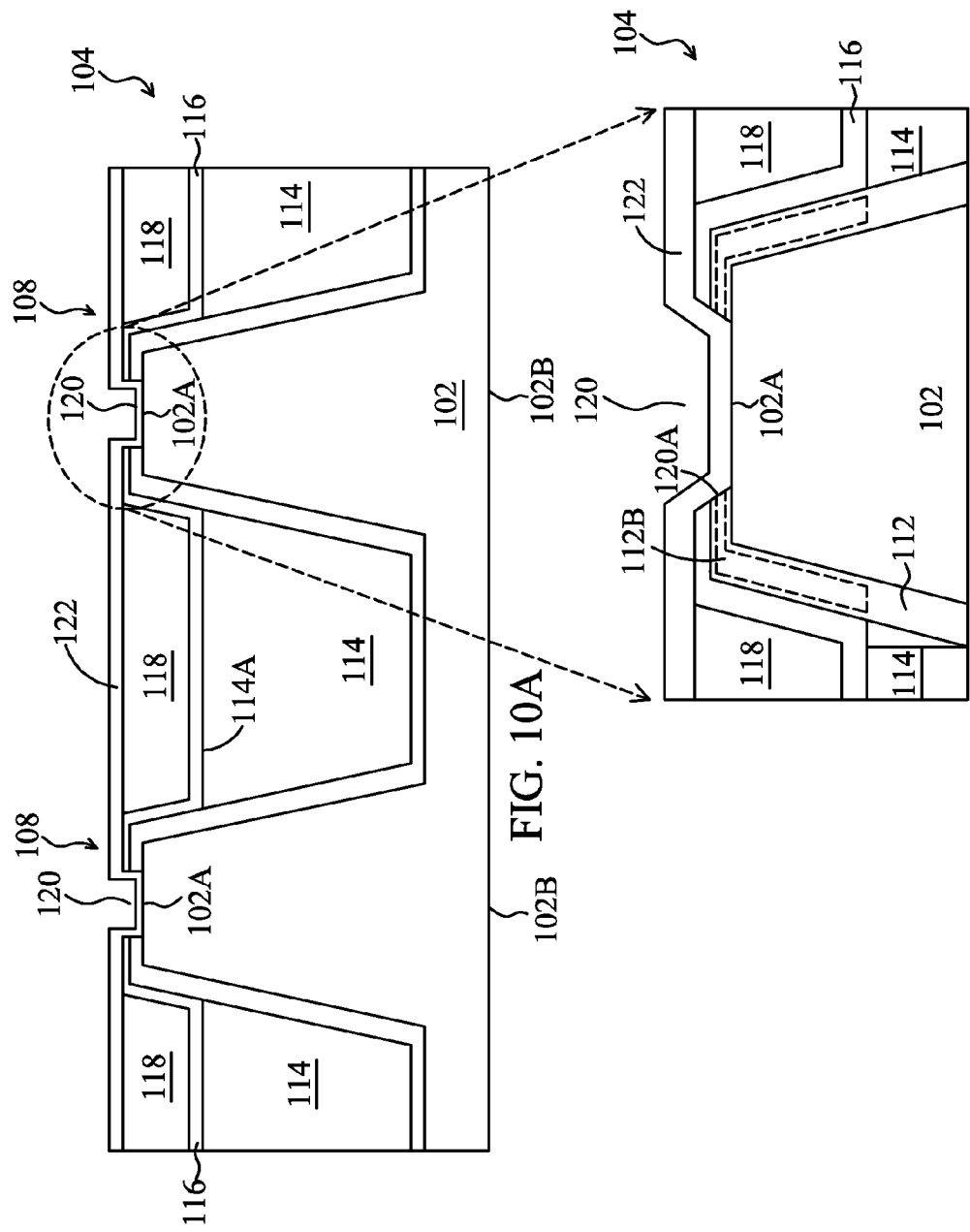

Referring to FIGS. 2 and 10A, the method 200 continues with operation 208 in which a second light reflecting layer is deposited over the first opening and the partially exposed top surface of each mesa. The second light reflecting layer is an opaque or reflective material. The second light reflecting layer may be compatible (e.g., friendly) for bio-entity binding. In some embodiments, the second light reflecting layer includes a metallic material such as aluminum, copper, gold, silver, chromium, titanium or mixtures thereof. The second light reflecting layer may be formed by a suitable process, such as physical vapor deposition (PVD), CVD or atomic layer deposition (ALD).

Referring the example of FIG. 10A, a second light reflecting layer 122 is deposited over the structure 104 of the biological chip in FIG. 9A. The second light reflecting layer 122 conformally covers the planarized sacrificial layer 118, the tapered sidewall 120A of the first openings 120 and the exposed portion of the top surface 102A of each mesa 108. FIG. 10B illustrates an enlarged cross-sectional view of a portion of the structure 104 of the biological chip in FIG. 10A. In at least one example, the second light reflecting layer 122 has a thickness from about 700 Å to about 1600 Å. Advantageously, the tapered sidewall 120A of the first opening 120 improves the step coverage of the following second light reflecting layer 122 deposition, prevents the second light reflecting layer 122 tends to overhang at the top corner of the first opening 120 and reduces the chance to seal the first opening 120 prematurely with a void formed under the overhang.

Figures 11A, 11B:
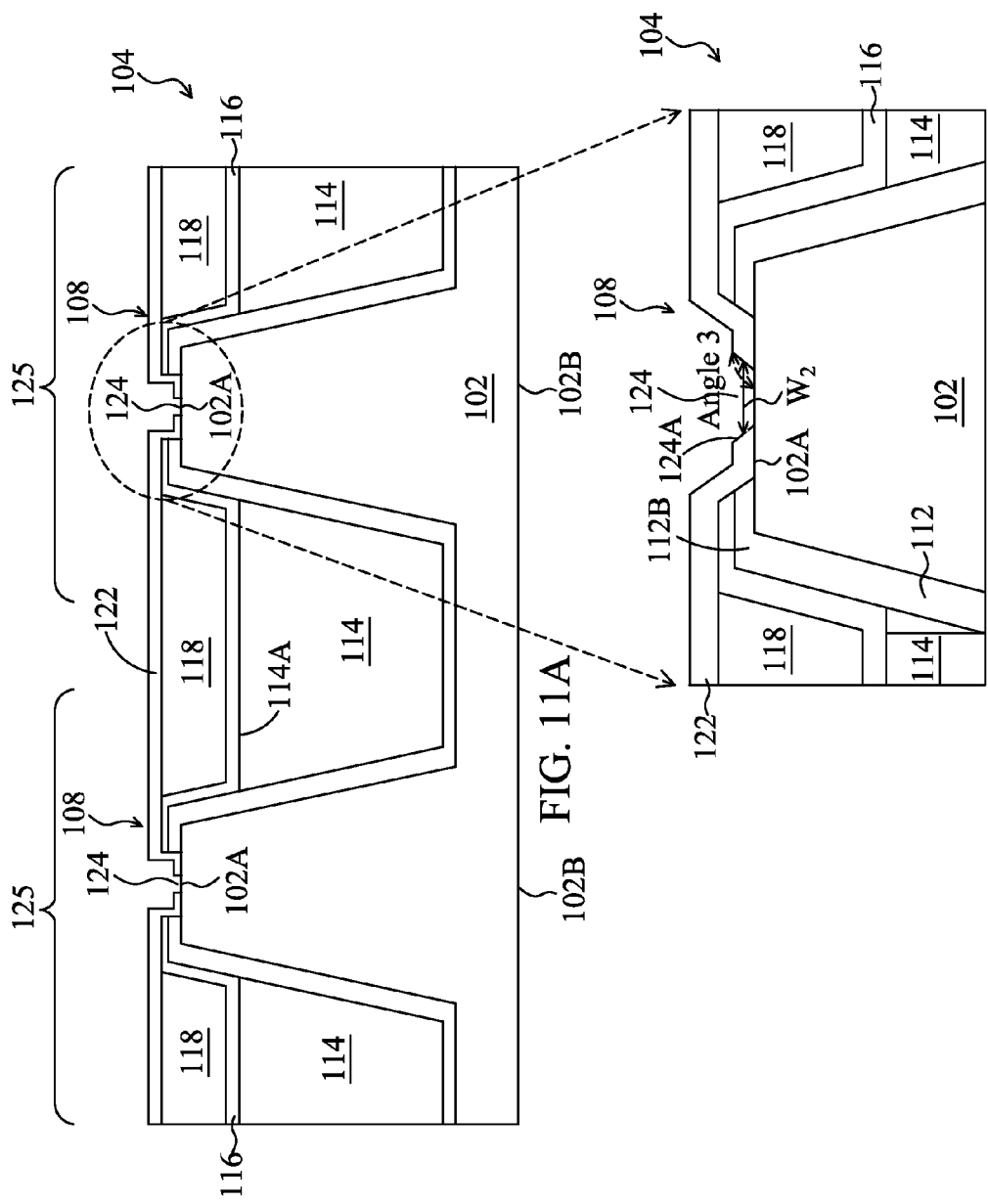

Referring to FIGS. 2 and 11A, the method 200 continues with operation 209 in which a second opening is formed in the second light reflecting layer to partially expose the top surface of each mesa. The second opening forming operation may be formed by using a suitable photolithography process and etching processes to remove a portion of the second light reflecting layer to define a second opening.

Referring the example of FIG. 11A, a second opening 124 in formed in the second light reflecting layer 122 to partially expose the top surface 102A of each mesa 108. FIG. 11B illustrates an enlarged cross-sectional view of a portion of the structure 104 of the biological chip in FIG. 11A. As shown in FIG. 11B, the second opening 124 has a tapered sidewall 124A with an interior angle, Angle 3, between the top surface 102A and the tapered sidewall 124A, in a range from about 90° to about 145°. In some embodiments, the second light reflecting layer 122 is aluminum. The aluminum layer is etched with a plasma process in a $BCl_3/Cl_2$ ambient environment. A gas ratio of $BCl_3/Cl_2$ is in a range of about 0.5 to about 1.3 for the tapered sidewall 124A. The second opening 124 is capable of containing an observed analyte. The analyte may include an enzyme, an antibody, a ligand, a peptide, an oligonucleotide, a cell of an organ, an organism or a piece of tissue. In at least one example, the second opening 124 has a width $W_2$ less than the width $W_1$ of the first opening 120. In at least another example, the width $W_2$ of the second opening 124 larger than the width $W_1$ of the first opening 120. In at least another example, the width $W_2$ of the second opening 124 is in a range from about 120 nm to about 160 nm. In at least another example, the width $W_2$ of the second opening 124 is capable of containing only one molecule of the analyte. The width $W_2$ contains a single DNA (deoxyribonucleic acid) polymerase within the second opening 124. After the operation 209, a biological sensing structure 125 having a micro-mirror is formed in the structure 104 of biological chip. In one embodiment, a plurality of biological sensing structures 125 are formed in an arrangement of an array on the structure 104 of the biological chip as shown in FIG. 12. A portion of the top surface 102A of each mesa 108 is exposed by the second opening 124 while other portions of the structure 104 of the biological chip covered by the second light reflecting layer 122.

In some embodiments, further process steps are optionally included after the operation 209. In some embodiments, a mechanically sawing or a laser sawing is performed along the scribe lines 106 of the wafer 100 and the substrate 102 are sawed into individual biological chips 103.

FIG. 13 illustrates an enlarged cross-sectional view of a biological sensing structure 125 in an operation of detecting biomolecules. The biological sensing structure 125 includes a mesa 108 integrally connected a portion of a substrate 102. The mesa 108 has the top surface 102A and the sidewall surface 110A adjacent to the top surface 102A. A first light reflecting layer 112 is disposed over the top surface 102A and the sidewall surface 110A of the mesa 108. The mesa 108 and the first light reflecting layer 112 disposed on the outside surface (102A and 110A) of the mesa 108 is configured as a micro-minor. A filling material 114 surrounds the mesa 108. The mesa 108 protrudes from a top surface 114A of the filling material 114. The stop layer 116 is disposed over the filling material 114 and the second portion of the first reflecting layer 112. The sacrificial layer 118 is disposed over the first portion of the stop layer 116 and exposes the second portion of the stop layer 116. The second light reflecting layer 122 is disposed over the second portion of the stop layer 116 and a portion of the top surface 102A of the mesa 108. The opening 124 is disposed in the second light reflecting layer 122 to partially expose the portion of the top surface 102A of the mesa 108. During the detecting operation, an analyte 126 is disposed in the second opening 124 of the biological sensing structure 125. The analyte 126 may include an enzyme, an antibody, a ligand, a peptide, an oligonucleotide, a cell of an organ, an organism or piece of tissue. A source of excitation radiation (not shown) generates radiation incident on the analyte 126. The analyte 126 may emit a light output 128 to the underneath micro-minor. The micro-mirror reflects the light output 128 and conveys the light output 128 to a detector 127 below the bottom surface 102B of substrate 102. The detector 127 collects the light output 128 and stores the light output 128 in a storage apparatus for analysis. The first light reflecting layer 112 may enhance the reflectivity of the outside surface (102A and 110A) of the mesa 108. The second opening 124 in the second light reflecting layer 122 confines the analyte 126 within the opening 124. The second light reflecting layer 122 on the top surface 102A of the mesa 108 also reflects the light output 128 to the detector 127.

Various embodiments of the present disclosure may be used to improve the performance of a biological chip having a biological sensing structure. For example, the stop layer 116 improves the uniformity of the planarized surface of the sacrificial layer 118. The planarized sacrificial layer 118 and the top surface of the stop layer 116 over the mesas 108 form the smooth new surface. The smooth new surface enhances capability to achieve a better resolution of the following lithography process on the new surface. The tapered sidewall 120A of the first opening 120 improves the step coverage of the following second light reflecting layer 122 deposition and prevents the second light reflecting layer 122 from overhanging at the top corner of the first opening 120. Due to the better resolution of the lithography process in defining the patterns of the second openings 124, the dimension of the second openings 124 among the biological chips 104 on the same wafer 100 could be accurately controlled during the etching process. The electrical or optical performances of each biological sensing structure 125 in the same biological chip 104 or the same wafer 100 could be tightly binned.

One aspect of this description relates to a biological sensing structure. The biological sensing structure includes a mesa integrally connected a portion of a substrate, wherein the mesa has a top surface and a sidewall surface adjacent to the top surface. The biological sensing structure further includes a first light reflecting layer disposed over the top surface and the sidewall surface of the mesa. The biological sensing structure further includes a filling material surrounding the mesa, wherein the mesa protrudes from a top surface of the filling material. The biological sensing structure further includes a stop layer disposed over the filling material and a portion of the first light reflecting layer. The biological sensing structure further includes a sacrificial layer disposed over a first portion of the stop layer and exposing a second portion of the stop layer. The biological sensing structure further includes a second light reflecting layer disposed over the second portion of the stop layer and a portion of the top surface of the mesa. The biological sensing structure further includes an opening disposed in the second light reflecting layer to partially expose the top surface of the mesa.

Another aspect of this description relates to a biological sensing array. The biological sensing array includes a plurality of mesas in a substrate, wherein each of the plurality of mesas has a top surface and a sidewall surface adjacent to the top surface. The biological sensing array further includes a first light reflecting layer covering the top surface and the sidewall surface of each mesa of the plurality of mesas. The biological sensing array further includes a filling material surrounding each mesa, wherein the filling material exposes a portion of the first light reflecting layer, and each mesa of the plurality of mesas protrudes from a top surface of the filling material by a step height W. The biological sensing array further includes a stop layer over the filling material and the exposed portion of the first light reflecting layer, wherein the stop layer has a thickness T less than the step height W. The biological sensing array further includes a sacrificial layer over the stop layer, wherein the sacrificial layer partially exposes the stop layer. The biological sensing array further includes a first opening in the stop layer and the first light reflecting layer, the first opening partially exposing the top surface of each mesa of the plurality of mesas, and the first opening includes a width $W_1$. The biological sensing array further includes a second light reflecting layer over at least the first opening and the partially exposed top surface of each mesa. The biological sensing array further includes a second opening in the second light reflecting layer to partially expose the top surface of each mesa, wherein the second opening includes a width $W_2$ less than the width $W_1$.

Still another aspect of this description relates to a biological sensing structure. The biological sensing structure includes a mesa in a substrate; and a first light reflecting layer covering a top surface and sidewall surface of the mesa. The biological sensing structure further includes a filling material over a first portion of the first light reflecting layer, wherein the filling material exposes a second portion of the first light reflecting layer. The biological sensing structure further includes a first opening in the first light reflecting layer, wherein the first opening exposes a first portion of the top surface of the mesa. The biological sensing structure further includes a second light reflecting layer over the first opening, wherein the second light reflecting layer exposes a portion of the top surface of the mesa. The biological sensing structure further includes a second opening in the second light reflecting layer, wherein the second opening exposes a second portion of the top surface of the mesa.

Although the embodiments and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed:

1. A biological sensing structure, comprising:
    a mesa integrally connected a portion of a substrate, wherein the mesa has a top surface and a sidewall surface adjacent to the top surface;
    a first light reflecting layer disposed over the top surface and the sidewall surface of the mesa;
    a filling material surrounding the mesa, wherein the mesa protrudes from a top surface of the filling material;
    a stop layer disposed over the filling material and a portion of the first light reflecting layer;
    a sacrificial layer disposed over a first portion of the stop layer and exposing a second portion of the stop layer;
    a second light reflecting layer disposed over the second portion of the stop layer and a portion of the top surface of the mesa; and
    an opening disposed in the second light reflecting layer to partially expose the top surface of the mesa.

2. The biological sensing structure of claim 1, wherein the opening is configured to receive an analyte.

3. The biological sensing structure of claim 1, wherein an angle between a sidewall of the second light reflecting layer adjacent to the opening and the top surface of the mesa ranges from 90-degrees to 145-degrees.

4. The biological sensing structure of claim 1, wherein a second opening is in the first light reflecting layer over the top surface of the mesa.

5. The biological sensing structure of claim 4, wherein a width of the second opening is less than a width of the opening in the second light reflecting layer.

6. The biological sensing structure of claim 4, wherein a width of the second opening is greater than a width of the opening in the second light reflecting layer.

7. The biological sensing structure of claim 4, wherein the second opening has tapered sidewalls.

8. The biological sensing structure of claim 1, wherein the first reflecting layer has a thickness ranging from 1000 angstroms to 3000 angstroms.

9. The biological sensing structure of claim 1, wherein a ratio between a depth from a top surface of the first light reflecting layer over the top surface of the mesa to a top surface of the filling material and a thickness of the stop layer is greater than 5.

10. The biological sensing structure of claim 1, wherein the stop layer is over a top surface of the first reflecting layer above the top surface of the mesa.

11. A biological sensing array comprising:
    a plurality of mesas in a substrate, wherein each of the plurality of mesas has a top surface and a sidewall surface adjacent to the top surface;
    a first light reflecting layer covering the top surface and the sidewall surface of each mesa of the plurality of mesas;
    a filling material surrounding each mesa, wherein the filling material exposes a portion of the first light reflecting layer, and each mesa of the plurality of mesas protrudes from a top surface of the filling material by a step height W;
    a stop layer over the filling material and the exposed portion of the first light reflecting layer, wherein the stop layer has a thickness T less than the step height W;
    a sacrificial layer over the stop layer, wherein the sacrificial layer partially exposes the stop layer;
    a first opening in the stop layer and the first light reflecting layer, the first opening partially exposing the top surface of each mesa of the plurality of mesas, and the first opening includes a width $W_1$;
    a second light reflecting layer over at least the first opening and the partially exposed top surface of each mesa; and
    a second opening in the second light reflecting layer to partially expose the top surface of each mesa, wherein the second opening includes a width $W_2$ less than the width $W_1$.

12. The biological sensing array of claim 11, wherein the stop layer is between a top surface of the first light reflecting layer and the second light reflecting layer.

13. The biological sensing array of claim 11, further comprising a detector on a surface of the substrate opposite the plurality of mesas.

14. The biological sensing array of claim 11, wherein the second light reflecting layer contacts the top surface of each mesa of the plurality of mesas.

15. The biological sensing array of claim 11, wherein the width $W_2$ is in a range from 120 nm to 160 nm.

16. A biological sensing structure comprising:
    a mesa in a substrate;
    a first light reflecting layer over a top surface and sidewall surface of the mesa;
    a filling material over a first portion of the first light reflecting layer, wherein the filling material exposes an upper surface and sidewalls of a second portion of the first light reflecting layer;
    a first opening in the first light reflecting layer, wherein the first opening exposes a first portion of the top surface of the mesa;
    a second light reflecting layer over the first opening, wherein the second light reflecting layer exposes a portion of the top surface of the mesa; and
    a second opening in the second light reflecting layer, wherein the second opening exposes a second portion of the top surface of the mesa.

17. The biological sensing structure of claim 16, wherein sidewalls of the second light reflecting layer adjacent to the second opening are tapered.

18. The biological sensing structure of claim 16, wherein an inside angle between a sidewall of the mesa and a plane of a top surface of the substrate ranges from 60-degrees to 85-degrees.

19. The biological sensing structure of claim 18, wherein a height of the mesa above the top surface of the substrate ranges from 6 microns to 7 microns.

20. The biological sensing structure of claim 16, wherein the mesa comprises at least one of quartz, sapphire, or fused silica.

* * * * *